United States Patent [19]

Augustine et al.

[11] Patent Number: 5,324,320
[45] Date of Patent: * Jun. 28, 1994

[54] THERMAL BLANKET

[75] Inventors: Scott D. Augustine; Douglas J. Augustine, both of Blue Springs, Mo.

[73] Assignee: Augustine Medical, Inc., Eden Prairie, Minn.

[ * ] Notice: The portion of the term of this patent subsequent to Feb. 9, 2010 has been disclaimed.

[21] Appl. No.: 703,592

[22] Filed: May 20, 1991

Related U.S. Application Data

[63] Continuation of Ser. No. 227,189, Aug. 2, 1988, abandoned, which is a continuation-in-part of Ser. No. 104,682, Oct. 5, 1987, abandoned.

[51] Int. Cl.$^5$ .............................................. A61F 7/00
[52] U.S. Cl. ................................. 607/107; 165/46; 5/482
[58] Field of Search .................. 219/12; 34/98, 99; 128/367–369, 373, 400, 402, 403, 379, 380; 62/259.3; 165/46; 5/482, 485

[56] References Cited

U.S. PATENT DOCUMENTS

| | | | |
|---|---|---|---|
| 2,110,022 | 3/1938 | Kliesrath | 128/400 |
| 2,512,559 | 6/1950 | Williams | 5/482 |
| 2,601,189 | 6/1952 | Wales | 5/482 |
| 3,691,646 | 9/1972 | Ruffolo | 34/99 |
| 3,714,947 | 2/1973 | Hardy | 128/400 |
| 4,572,188 | 2/1986 | Augustine et al. | 128/380 |
| 4,660,388 | 4/1987 | Greene | 5/485 |

FOREIGN PATENT DOCUMENTS

| | | | |
|---|---|---|---|
| 8503216 | 8/1985 | European Pat. Off. | 128/400 |
| 3308553 | 9/1984 | Fed. Rep. of Germany . | |

OTHER PUBLICATIONS

Search Report in EPO Patent Application EPO 88309191.0.

Primary Examiner—Mark S. Graham
Attorney, Agent, or Firm—Baker, Maxham, Jester & Meador

[57] ABSTRACT

A thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally-controlled inflating medium from the covering. Exhaust port openings are provided at the edges of the covering to vent the inflating medium, which enhances circulation of the thermally-controlled medium through the cover. An uninflatable section is provided at the head end, together with an absorbent bib attached to the covering, adjacent the uninflatable section. When inflated, the thermal blanket self-erects and provides a bath of thermally-controlled inflating medium to the interior of the erected structure. The enhanced circulation of the medium through the covers maintains a relatively high average temperature under the blanket and a relatively uniform distribution of temperature in the inflating medium which is exhausted through the apertures into the structure's interior. When the structure covers a patient, the uninflatable section provides a relatively unobstructed view of the patient's face, while the absorbent bib maintains a relatively sanitary environment in the area beneath the patient's head.

24 Claims, 2 Drawing Sheets

THERMAL BLANKET

This is a continuation (FILE WRAPPER) of application Ser. No. 07/227,189 filed Aug. 2, 1988, abandoned, which is a continuation-in-part of application Ser. No. 07/104,682 filed Oct. 5, 1987, abandoned.

BACKGROUND OF THE INVENTION

This invention relates to thermal blankets used in a medical setting to deliver a bath of a thermally-controlled medium to a patient.

The thermal blanket prior art is best expressed in our prior U.S. Pat. No. 4,572,188 entitled "AIRFLOW COVER FOR CONTROLLING BODY TEMPERATURE." In our prior patent, a self-erecting, inflatable airflow cover is inflated by the introduction into the cover of a thermally-controlled inflating medium, such as warmed air. When inflated, the cover self-erects about a patient, thereby creating an ambient environment about the patient, the thermal characteristics of which are determined by the temperature of the inflating medium. Holes on the underside of our prior art airflow cover exhaust the thermally-controlled, inflating medium from inside the cover to the interior of the erected structure. Our airflow cover is intended for the treatment of hypothermia, as might occur postoperatively.

Evaluation of our airflow cover by skilled practitioners has resulted in general approbation: the opinion is that the airflow cover efficiently and effectively accomplishes its purpose of giving a thermally-controlled bath. We have realized, however, that, while our prior art airflow cover achieves its objective, certain improvements to it are necessary in order to realize additional clinical objectives and to enjoy further advantages in its use.

SUMMARY OF THE INVENTION

We have improved the clinical usefulness of our self-erecting airflow cover by observing that controlling the contour of its inflatable portion at its head end to define a generally concave non-inflatable portion will permit a care giver to more easily observe a patient's head, face, neck and chest. Further, we have observed that limited venting of the thermally controlled inflating medium from the edges of the cover results in more efficient, more uniform heating within the cover. We have also observed that it is good clinical practice to keep the area of the care site in the vicinity of the patient's head and face as clean as possible.

These three observations have resulted in an improved thermal blanket in which a self-erecting inflatable covering has a head end, a foot end, two edges, and an undersurface. An inflating inlet adjacent said foot end admits a thermally-controlled inflating medium into the covering. An aperture array on the undersurface of the covering exhausts the thermally-controlled inflating medium from the covering into the structure created when the covering self-erects upon inflation. The improvements to this basic structural complement include an uninflatable section at the head end of the covering, exhaust port openings at the edges of the covering, an absorbent bib attached to the covering at the head end adjacent the uninflatable section, and structural features that make the covering simple and economical to produce.

With these improvements, the thermal blanket, when inflated and erected over a patient, delivers the thermally-controlled inflating medium into the interior of the structure covering the patient, thereby thermally bathing the patient. The first improvement permits full viewing of the head and face of the patient from almost any aspect around the thermal blanket. The exhaust port openings increase the rate of circulation of the inflating medium within the blanket, thereby increasing the temperature within the structure and making the temperature distribution more uniform. The absorbent bib soaks up and retains liquids which might otherwise spread over the care site in the area of a patient's head. Such liquids can include the patient's own perspiration, blood, vomit, saliva, or liquids which are administered to the patient. The absorbent bib also acts to some extent to seal the head end of the inflated structure.

From another aspect, the invention is a thermal blanket for covering and bathing a person in a thermally-controlled medium. The thermal blanket includes a flexible base sheet having a head end, a foot end, two edges, and a plurality of apertures opening between the first and second surface of the base sheet. An overlying material sheet is attached to the first surface of the base sheet by a plurality of discontinuous seams which form the material sheet into a plurality of substantially parallel, inflatable chambers. A continuous seam is provided between the material sheet and the base sheet at the head end to form a non-inflatable viewing recess at the head end. Exhaust port openings are provided through the material sheet to vent the medium from the chambers away from the base sheet. An absorbent bib is attached to the head end in the vicinity of the viewing recess.

Therefore the invention accomplishes the important objective of providing a self-erecting, inflatable thermal blanket that permits a relatively unobstructed view of a patient's head and face when in use.

Another objective is the efficient and uniform heating of the interior of the structure created when the blanket is inflated with a heat inflating medium.

A signal advantage of the invention is the provision of such a blanket with a means for maintaining the cleanliness of the care site in the vicinity of the patient's head and face.

The advantageous simplified structure of the thermal blanket make its production straightforward and economical.

These and other important objectives and advantages will become evident when the detailed description of the invention is read with reference to the below-summarized drawings, in which.

DETAILED DESCRIPTION OF THE PREFERRED EMBODIMENT

When used herein, the term "thermal blanket" is intended to be interchangeable with, but not necessarily limited by, the term "airflow cover" used in our U.S. Pat. No. 4,572,188, which is incorporated herein in its entirety by reference. In this description, the term "thermal blanket" is meant to invoke a self-erecting, inflatable structure for delivering a thermally-controlled inflating medium to the interior of the structure created when the thermal blanket is inflated. The purpose of the thermal blanket is to efficiently administer a uniformly thermally-controlled bath of the inflating medium to a patient within the erected structure.

Figure 1:
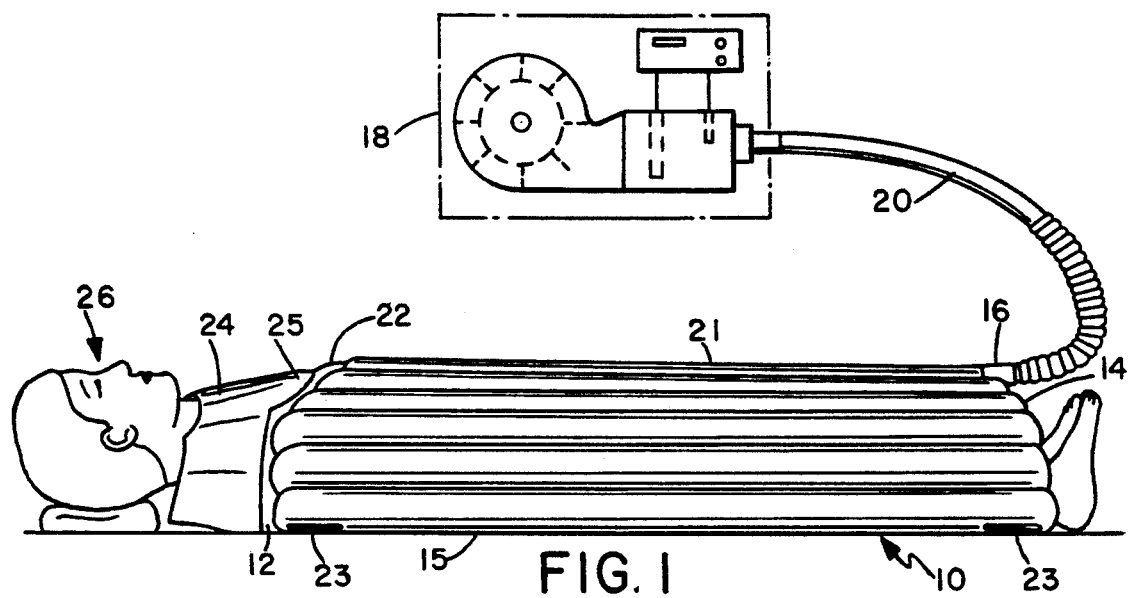
FIG. 1 is a side elevation view of the thermal blanket in use, with associated thermal apparatus indicated schematically.

Our invention is illustrated as we intend for it to be used in FIG. 1. In FIG. 1, a self-erecting, inflatable thermal blanket 10 has a head end 12, a foot end 14 and two lateral edges, one indicated by 15. An inflation inlet cuff 16 is connected to a heater/blower assembly 18 which provides a stream of heated air through a connecting hose 20. When the heater/blower 18 is operated, the stream of heated air flows through the inflating hose 20 into the thermal blanket 10 through the inflation cuff 16. When the blanket is inflated, it erects itself into a Quonset hut-like structure with a quilted upper surface 21. As described below, a pattern of apertures on the undersurface of the blanket (not shown in FIG. 1) delivers the inflating heated air into the interior space enclosed by the erected thermal blanket.

The contour of the inflatable portion of the thermal blanket 10 is varied at the head end 12 of the blanket to provide a non-inflated blanket recess 22 in the quilted upper surface 21, which remains smooth and flat when the blanket is inflated and erected. Circulation of the heated air is accelerated through the thermal blanket by exhaust port openings in the upper surface, adjacent the lateral edges of the blanket. Two exhaust port openings are indicated by reference numeral 23. Further, a bib 24 made of an absorbent material is attached to the head end 12 of the thermal blanket in the vicinity of the non-inflated recess 22. In fact, as shown in FIG. 1 the bib 24 includes a semi-circular tab 25 that extends into the recess 22.

As illustrated in FIG. 1, the thermal blanket of the invention is inflated, erects itself into a bathing structure, and bathes a patient 26 with the thermally-controlled air used to inflate the structure. While the patient is being thermally bathed, the uninflated recess 22 permits observation of the patient's head, face, neck, and chest from almost any location with respect to the thermal blanket 10. Thus, if the patient is placed on a gurney or a bed, the head of which is against a wall, a care giver such as a nurse, intern, resident, or doctor, can keep the patient's face under observation from the foot end 14 of the thermal blanket 10. Respiration can be detected by the rise and fall of the bib and uninflated area, which rest directly on the patient's chest. Moreover, the bib 24 will provide an absorbent sink for stray, unconfined liquids in the area of the patient's head or at the head end 12 of the thermal blanket 10.

Figure 2:
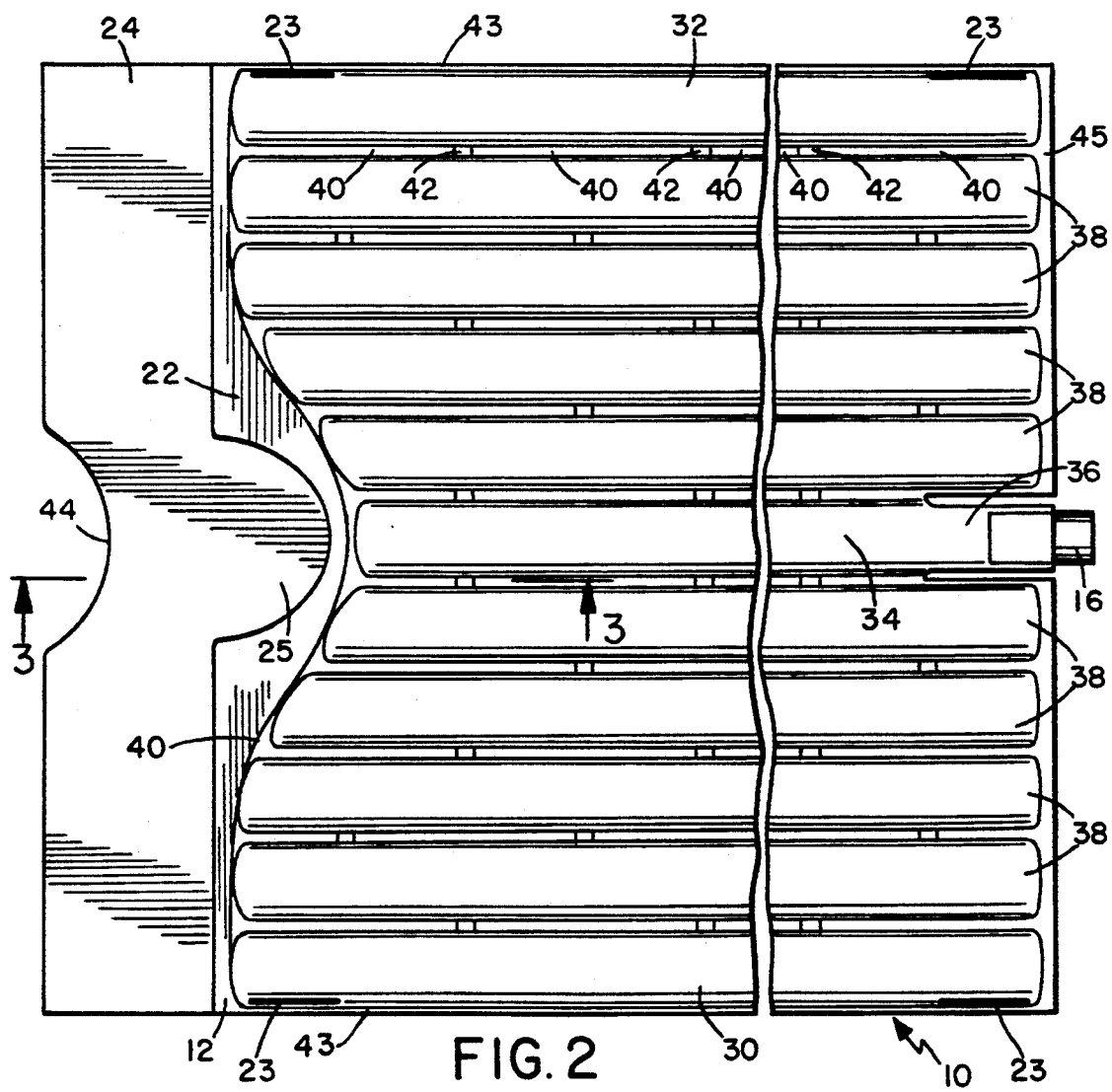
FIG. 2 is an enlarged top plan view of the thermal blanket opened flat.

FIG. 2 is a plan view of the thermal blanket 10 opened flat to show details of its structure. FIG. 2 illustrates the upper surface of the thermal blanket, that is the side that is visible in FIG. 1. As seen, the upper surface consists of a parallel array of elongated tubes of which 30 and 32 are the lateralmost tubes, 34 is the center tube, and the tubes 38 are arrayed between one of the lateralmost tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the thermal blanket, when inflated, to assume a tubular structure on the upper surface, while the ports 42 permit full circulation of the inflating medium throughout the array of tubes. The foot-end seam 45 is continuous. The tubes are inflated through the center tube 34 which transitions to a port 36, through which the inflation cuff 16 is inserted. The edge seams 43 are discontinuous only at the exhaust port opening locations 23. A seal can be made between the inflation port 36 and the inflation cuff 16 by any conventional means, for example, an O-ring, or even tape. When the inflating medium is introduced into the center tube 34, it flows laterally from the center tube into all of the other tubes through the ports 42. Near the head end 12, a continuous seam 40 defines the forward end of all of the tubes, with the seam assuming a bell-curve shape. On the head end side of the seam 40, the thermal blanket 10 is uninflatable. The bell-shaped seam 40 thus defines the uninflatable area 22 at the head end of the thermal blanket 10, which is essentially coplanar with, or substantially parallel to, the underside of the blanket. As shown in FIG. 1, by virtue of its structural integration with the rest of the thermal blanket 10, the non-inflated recess extends over the upper chest of the patient 26 when the blanket is inflated. However, since the recess 22 is uninflated, it provides a wide-angled viewing gap in the inflated contour of the upper surface 21. The gap is filled by continuation of the underside of the blanket. It is also noted that the pattern of inflatable tubes can be replaced by other suitable patterns of communicating, inflatable chambers. The tubes are preferred since they impart strength and shape to the erected bathing structure; other inflatable structures are contemplated, however.

The absorbent bib has an indent 43 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
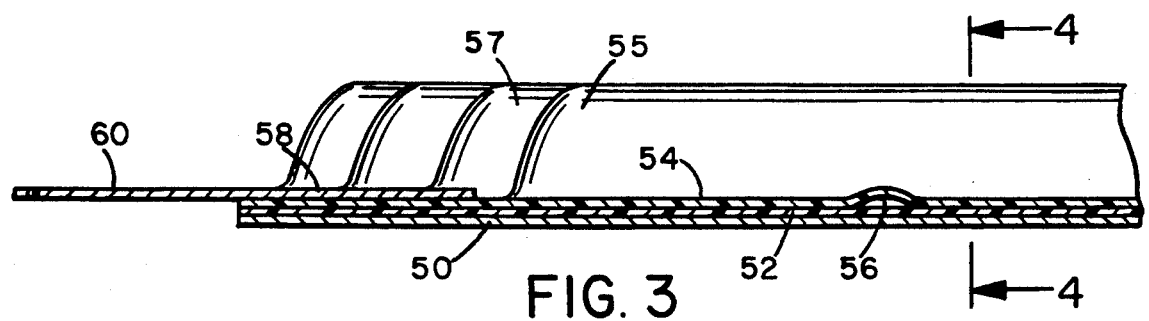
FIG. 3 is an enlarged sectional view taken along 3-3 of FIG. 2.
Figure 4:
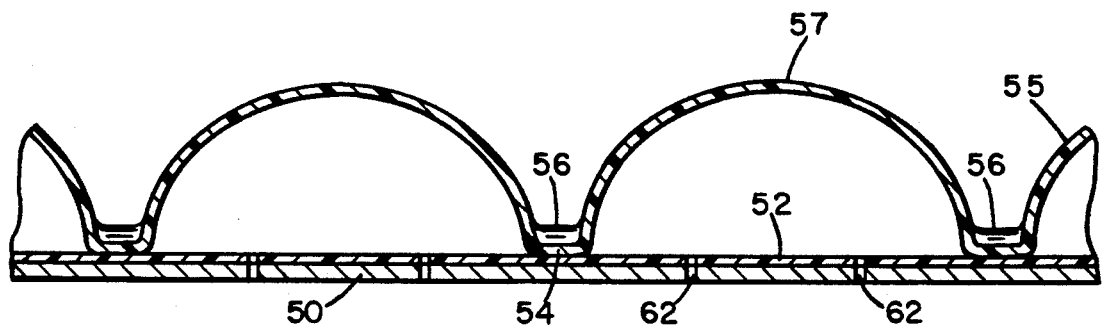
FIG. 4 is a further enlarged sectional view taken along line 4—4 of FIG. 3.

Construction details of the thermal blanket 10 are illustrated in FIGS. 3 and 4. The thermal blanket 10 is assembled from a base sheet consisting of an underside layer 50 formed from flexible material capable of bonding to a layer 52 of heat-sealable plastic. For the layers 50 and 52, we have used a stratum of absorbent tissue paper prelaminated with a layer of heat-sealable plastic. Material of such construction is commercially available in production rolls and is used to make painters' drop cloths. The upper side of the thermal blanket consists of a sheet of plastic bonded to the plastic layer 52 by an interruptible heat-sealing process to form the interrupted seams, one of which is indicated by 54, and the inflatable tubes, one indicated by 55. As can be seen in FIG. 3, the interruption of the seam 54 forms a passageway 56 between adjacent tubes 55 and 57.

The absorbent bib and tab are shown in FIG. 3 as a single material layer 60/58. Alternatively, they may be formed from separate material sheets cut to the outlines illustrated in FIG. 2. The absorbent material forming the bib and tab can be bonded to the upper plastic layer by heat process or by gluing.

The inventors also contemplate deletion of the bib and tab. In this instance, the thermal blanket would still have the viewing recess, which would be defined by the continuous seam at the head end, and which would be filled with the forward portion of the base sheet.

Circulation of heated air through the blanket is enhanced by the exhaust port openings 23, which open through the upper plastic sheet sheet, which is heat sealed to the base of the blanket. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket. We have measured the temperature distribution within the thermal blanket for inflating air which is heated to a medium temperature range and for inflating air which is heated to a high temperature range. The results are provided in Table I for a blanket consisting of 13 tubes. Measurements of the temperature of air exhausted through underside apertures were made on the underside of each tube on one side of the blanket. The tubes are numbered 1-6, with 1 being the tube adjacent to the center tube, and tube 6 being the outermost tube adjacent on lateral edge of the blanket. Test apertures were made in the bottom of tube 6 only for the purposes of this test. As is evident, the distribution of temperature within the erected thermal blanket is more uniform when the exhaust port openings are provided. Further, provision of the exhaust ports also increases the average temperature within the erected structure of the blanket. Clearly, the provision of exhaust port openings at the lateral edges of the blanket delivers results which one would not expect when considering the operation of our thermal blanket with no exhaust port openings.

In our preferred embodiment, the exhaust port openings are slits in the edge seams of our blanket. These slits vary in length from 1¾ to 2 inches. Each edge seam is discontinuous approximately at each corner of the blanket so that inflating air is vented away from the underside of the erected blanket. This keeps the relatively "colder" air at the blanket edges from mixing with the relatively "hotter" air exhausted into the structure through the underside apertures. The result is a "flatter" temperature profile of air within the blanket than without the vents, which raises the average temperature within the erected structure and makes the temperature distribution in the structure more uniform. Resultantly, the clinical effect of the blanket is enhanced. Heating is better controlled, and more uniform, with greater comfort to the patient.

TABLE I

| TUBE NO. | MEDIUM TEMPERATURE RANGE | | HIGH TEMPERATURE RANGE | |
|---|---|---|---|---|
| | WITHOUT EXHAUST PORTS | WITH 2" EXHAUST PORTS | WITHOUT EXHAUST PORTS | WITH 2" EXHAUST PORTS |
| center (inlet) tube | 113.3° F. | 114.1° F. | 121.3° F. | 121.3° F. |
| Tube #1 | 109.9° | 112.3° | 117.3° | 117.7° |
| Tube #2 | 105.3° | 109.8° | 113.4° | 115.0° |
| Tube #3 | 103.2° | 107.1° | 111.0° | 113.3° |
| Tube #4 | 99.9° | 104.3° | 101.4° | 108.6° |
| Tube #5 | 97.2° | 100.0° | 95.7° | 104.4° |
| Tube #6 (outermost) | 85.2° | 95.8° | 89.6° | 99.4° |
| Average | 103.8° | 106.7° | 108.4° | 112.5° |
| temp. under cover | | | | |

Figure 5:
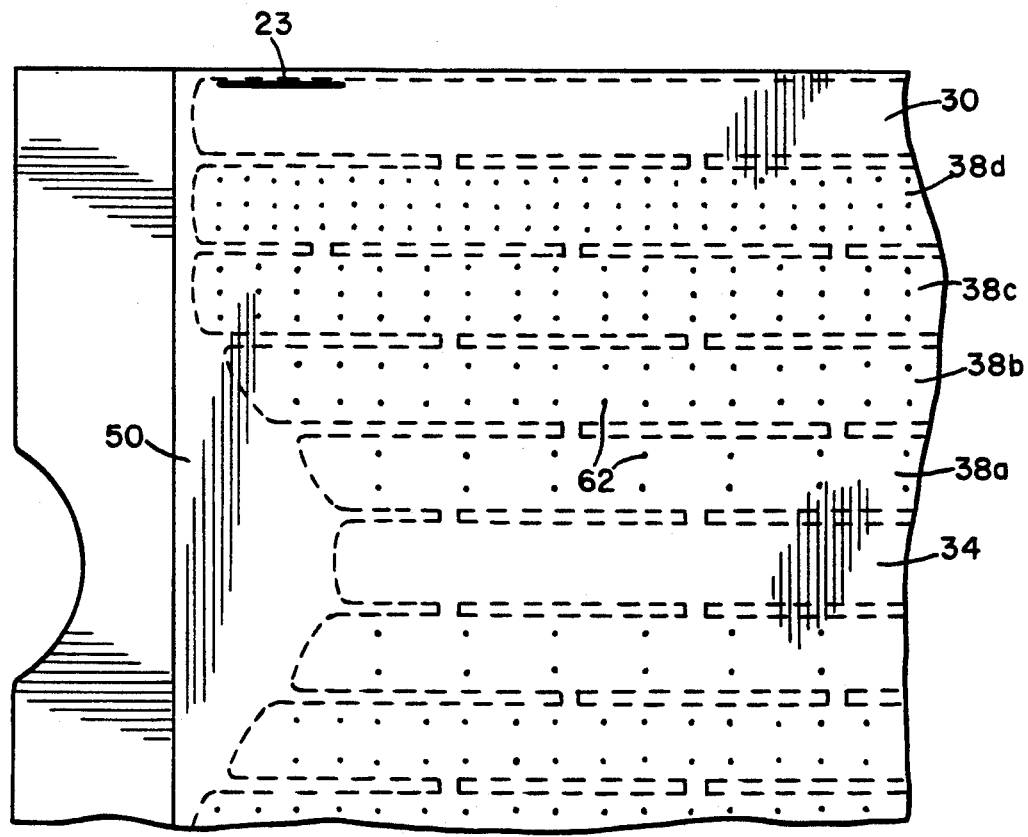
FIG. 5 is a partial underside view of the thermal blanket.

The thermal blanket of the invention is enabled to bathe a patient in the thermally-controlled inflating medium introduced into the upper side tubes by means of a plurality of apertures, 62 shown in FIGS. 4 and 5. The apertures extend through the underside of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateralmost tubes 30 and 32, or into the center tube 34. In addition, the apertures 62 are provided through the underside to the apertured tubes in a density which varies inversely with the proximity of the tube to the center tube 34. Thus, the hole density increases from the tube 38a through the tube 38d. Even with the exhaust port openings, the temperature of the inflating medium exhibits a drop from the center to the lateralmost tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the thermal blanket. Therefore, fewer apertures are required for the tubes near the center tube 34 to deliver the same amount of air as the relatively greater number of apertures in the tubes at a greater distance from the center tube 34.

The apertures comprise openings which can be of any appropriate shape. For example, we have produced blankets with elongated apertures, approximately ¼ inch in length.

Many modifications and variations of our invention will be evident to those skilled in the art. It is understood that such variations may deviate from specific teachings of this description without departing from the essence of the invention, which is expressed in the following claims.

We claim:

1. In a self-erecting, inflatable thermal blanket for covering and bathing a person in a thermally-controlled medium, the improvement comprising:

a flexible base sheet having a head end, a foot end, two edges, and a plurality of apertures;

an overlaying plastic sheet attached to a first surface of said base sheet by a plurality of discontinuous seams which form said plastic sheet into a plurality of communicating inflatable chambers, said apertures opening through said base sheet into said chambers;

a continuous seam between said plastic sheet and said base sheet at said head end which forms a non-inflatable viewing recess; and an exhaust vent in said overlaying plastic sheet and adjacent a first edge, opening from a first inflatable chamber adjacent said first edge, for venting an inflating medium away from said base sheet.

2. The self erecting, inflatable thermal blanket of claim 1 including an absorbent bid attached to the head end of said base sheet.

3. In a self-erecting, inflatable, convective thermal blanket for covering and bathing a person with a thermally-controlled, inflating medium wherein the improvement comprises:

a flexible base sheet having two ends and two edges;

a flexible material sheet attached to a first surface of said base sheet by a plurality of discontinuous seams which form a plurality of communicating, inflatable chambers between said flexible base sheet and said flexible material sheet;

a means for admitting an inflating medium into said chambers;

said flexible base sheet including means for permitting passage of said inflating medium from said chambers through said flexible bas sheet; and a vent means in said flexible material sheet adjacent a first edge of said flexible base sheet for circulating said inflating medium through said inflatable chambers by exhausting said inflating medium from a first inflatable chamber adjacent said first edge.

4. The thermal blanket of claim 3, wherein said flexible base sheet includes an undersheet of flexible fibrous material and a sheet of plastic material coextensive with, and attached to, said undersheet.

5. The thermal blanket of claim 4, wherein said discontinuous seams are substantially elongate seals, formed between said flexible material sheet and said flexible base sheet, which form said inflatable chambers into a plurality of mutually parallel, communicating tubular chambers extending between said two ends.

6. An inflatable, convective thermal blanket for covering and bathing a person in a thermally-controlled inflating medium, comprising:

a flexible base sheet having ahead end, a foot end, two edges, and a plurality of apertures;

an plastic sheet attached to a first surface of said base sheet by a plurality of discontinuous seams which form said plastic sheet into a plurality of communicating, inflatable chambers, said apertures opening through base sheet into said chambers; and an exhaust vent opening through said plastic sheet into a first inflatable chamber adjacent said first edge, for circulating an inflating medium through said inflatable chambers by venting said inflating medium from said first inflatable chamber.

7. In a self-erecting, inflatable thermal blanket for covering and bathing a person in a thermally-controlled inflating medium, the improvement comprising:

a flexible base sheet having a head end, a foot end, two edges, a plurality of apertures;

an overlaying flexible material sheet attached to a first surface of said base sheet by a plurality of discontinuous seams which form said overlaying material sheet into a plurality of communicating, inflatable chambers, said apertures opening through said base sheet into said chambers;

a continuous seam between said overlaying material sheet and said base sheet near said head end which closed ends of said inflatable chambers; and a non-inflatable section of said thermal blanket extending substantially between said continuous seam and said head end and including an end portion of said flexible base sheet.

8. The improvement of claim 7 wherein said base sheet includes an undersheet of flexible fibrous material and a sheet of plastic material co-extensive with, and attached to, said undersheet.

9. The improvement of claim 7 wherein said base sheet includes a multi-layered structure in which the bottom-most layer is a paper sheet bonded to an upper sheet of plastic material.

10. The improvement of claim 8 wherein said discontinuous seams are substantially elongate seals formed between said overlaying material sheet and said sheet of plastic material, and said continuous seam is an elongate seal which extend between said edges substantially transversely to said elongate seals.

11. The improvement of claim 8 wherein one of said discontinuous seams includes a sequence of co-linear seals extending substantially from said foot end to said continuous seam.

12. The improvement of claim 11 wherein said plurality of discontinuous seams form said overlaying material sheet into a plurality of mutually parallel, communicating tubular chambers.

13. The improvement of claim 7 including exhaust port openings through aid overlaying material sheet for circulating said inflating medium within said thermal blanket toward said two edges.

14. The improvement of claim 7 including a patterned array of apertures opening through said underside into said chambers, said patterned array comprising a density pattern in which the density of said apertures increases toward one of said edges.

15. The improvement of claim 12 including a patterned array of apertures, said apertures opening through said base sheet into said chambers, said patterned array comprising a density pattern in which the density of said apertures increases toward one of said edges.

16. The improvement of claim 15 wherein one of said tubular chambers is centrally positioned in said parallel tubular chambers and said density increases from said central position chamber toward one of said edges.

17. The improvement of claim 16 wherein no apertures open through said base sheet into said centrally positioned tubular chamber.

18. The improvement of claim 17 wherein no apertures open through said base sheet into a tubular chamber adjacent one of said edges.

19. An inflatable thermal blanket for convectively controlling the temperature of a human body, comprising:

a self-erecting, inflatable covering with a head end, a foot end, two edges, and an undersurface;

an inflating inlet for admitting a thermally controlled, inflating medium into said covering;

an array of apertures in said undersurface for exhausting a thermally controlled inflating medium from said covering to said undersurface;

means in said inflatable covering for equalizing the temperature of the thermally controlled inflating medium in said inflatable covering by circulating said inflating medium toward said two edges; and an inflatable extension in said inflatable covering at said end;

wherein said array of apertures is in a pattern which increases the density of said apertures from a central location on said undersurface in a direction toward a first one of said two edges.

20. The thermal blanket to claim 19 wherein the pattern increases the density of said apertures from said central location in a direction toward the second of said two edges.

21. A convective thermal blanket for being inflatably erected to enclose and bathe a person in a thermally-controlled inflating medium, comprising:
    flexible base sheet having a head end, a foot end, two edges, and a plurality of apertures, the base sheet including a first layer of non-plastic material and a second layer of plastic material attached to said first layer;
    an overlaying plastic sheet attached to said second layer of said base sheet by a plurality of discontinuous means which form said plastic sheet into a plurality of communicating, inflatable chambers, said apertures opening through said base sheet into said chambers;
    a continuous seal transverse to and closing ends of said inflatable chambers, the continuous seal being between said plastic sheet and said second layer of said base sheet near said head end; and
    an uninflatable viewing portion extending between said head end and said continuous seal, said viewing portion including respective extensions of said base sheet and said plastic sheet.

22. A self erecting, inflatable thermal blanket for covering and bathing a person in a thermally-controlled inflating medium, comprising:
    a flexible base sheet having a head end, a foot end, two edges, and a plurality of apertures;
    an overlaying flexible material sheet attached to a first surface of said base sheet by a plurality of discontinuous seams which form said overlaying material sheet int a plurality of communicating, inflatable chambers, said apertures opening through said base sheet into said chambers; and
    means in an inflatable chamber and responsive to a thermally-controlled inflatable medium for equalizing the temperature of said thermally-controlled inflating medium within said chambers;
    wherein said means includes vent ports in said inflatable chamber, said vent ports through said overlaying flexible material sheet.

23. A self erecting, inflatable thermal blanket for covering and bathing a person in a thermally-controlled inflating medium, comprising:
    a flexible base sheet having two ends, two edges, and a plurality of apertures;
    an overlaying flexible material sheet attached to a first surface of said base sheet by a plurality of discontinuous seams which extend substantially between said two ends an at least two continuous seams which extend substantially between said edges, said discontinuous and continuous seams forming said overlaying material sheet into a plurality of communicating, inflatable chambers, said apertures opening through said base sheet into said chambers; and
    means in a first inflatable chamber for equalizing the temperatures of said thermally-controlled inflating medium by circulating said thermally-controlled inflating medium within said chambers to said edges;
    wherein said means includes an opening in said overlaying plastic sheet into said first chamber.

24. An inflatable, self-erecting thermal blanket for bathing a person in an inflating medium, comprising:
    a flexible undersheet;
    the flexible undersheet including a layer of a first flexible material;
    the flexible undersheet including a layer of a second flexible material bonded to the layer of first flexible material;
    an overlaying, flexible material sheet attached to the layer of second flexible material by a plurality of discontinuous seams which form the overlaying material sheet into a plurality of communicating, inflatable chambers;
    a plurality of apertures opening through the layer of first flexible material and the layer of second flexible material of the undersheet into the chambers;
    means for admitting a thermally-controlled, inflating medium into the chambers; and
    a vent port opening through the overlaying material sheet into one of the chambers for circulating a thermally-controlled, inflatable medium toward one of said edges.

* * * * *

UNITED STATES PATENT AND TRADEMARK OFFICE
CERTIFICATE OF CORRECTION

PATENT NO. : 5,324,320
DATED : June 28, 1994
INVENTOR(S) : Scott D. Augustine, et. al.

It is certified that error appears in the above-indentified patent and that said Letters Patent is hereby corrected as shown below:

Column 7, line 6, change "bid" to --bib--.
    line 22, change "bas" to --base--;
    line 41, change "ahead"to -- a head--;
    line 43, change "an" to --a--;
    line 57, insert --and-- between the comma and "a"; and
    line 66, change "closed" to --closes--.
Column 8, line 15, change "extend" to extends--.
Column 10, line 12, change "an" to --and--.

Signed and Sealed this

Seventh Day of February, 1995

Attest:

BRUCE LEHMAN

*Attesting Officer*     *Commissioner of Patents and Trademarks*